United States Patent [19]
Naraghi

[11] Patent Number: 5,084,047
[45] Date of Patent: Jan. 28, 1992

[54] FRACTURE REDUCING APPARATUS

[76] Inventor: Fred F. Naraghi, 8161 Skyline Blvd., Oakland, Calif. 94611

[21] Appl. No.: 675,169

[22] Filed: Mar. 26, 1991

[51] Int. Cl.⁵ .................................. A61F 5/01
[52] U.S. Cl. ............................. 606/57; 606/53; 128/83
[58] Field of Search ............... 606/53, 54, 57, 58, 606/59; 128/83

[56] References Cited

U.S. PATENT DOCUMENTS

| | | | |
|---|---|---|---|
| 1,308,799 | 7/1919 | Masland | 606/86 |
| 2,631,585 | 3/1953 | Siebrandt | 606/86 |
| 3,693,617 | 9/1972 | Trott | 128/84 B |
| 4,098,269 | 7/1978 | Judet | 606/59 X |
| 4,360,012 | 11/1982 | McHarrie et al. | 606/54 |
| 4,471,768 | 9/1984 | Ciullo | 128/83 |
| 4,558,697 | 12/1985 | Wu | 606/86 |

FOREIGN PATENT DOCUMENTS

| | | | |
|---|---|---|---|
| 0538932 | 11/1931 | Fed. Rep. of Germany | 606/57 |
| 0839509 | 6/1981 | U.S.S.R. | 606/86 |
| 0891082 | 12/1981 | U.S.S.R. | 606/86 |
| 1510843 | 9/1989 | U.S.S.R. | 606/53 |
| 8905126 | 6/1989 | World Int. Prop. O. | 606/59 |

Primary Examiner—Robert A. Hafer
Assistant Examiner—Sam Rimmell

[57] ABSTRACT

A fracture reducing apparatus for achieving and maintaining fracture reduction having three side arms which are threadedly connected to two main arms. A knob pivotally connects the two main arms and maintains their relative position with respect to one another. The side arms of the apparatus distribute the surgeon's manipulating force to three points along the surface of the fractured limb and when the reduction is achieved, the knob is tightened to maintain the reduction, thus freeing surgeon's hands to apply the fixation, or to completely move out of the field of x-ray exposure.

1 Claim, 4 Drawing Sheets

FRACTURE REDUCING APPARATUS

BACKGROUND OF INVENTION

1. Field of Invention

This invention relates in general to Orthopedic Surgery and more specifically to reducing of bone fractures from the surface of the limb.

2. Description of Prior Art

Setting of fractures, also known as fracture reduction, generally requires the application of traction to the fractured limb and the manipulation of the bone fragments, under x-ray guidance, to align the bone. In fractures of the long bones, such as femur, due to the tremendous forces exerted by the muscles on the bone, reduction of the fractured bone often requires maneuvering of the fragments with large counteracting forces applied by the orthopedic surgeon and the assistants at multiple locations of the limb. In the course of this procedure, whether it is done in the Emergency Room or under sterile conditions in the Operating Room with fluoroscopy in use, the surgeon must overcome several important problems:

(a) While the fracture is being reduced, in order to maintain the relative alignment of the bone fragments, the surgeon and assistants must continually apply the counteracting forces until a cast or an intramedullary fixation is put in place.

(b) During reduction, the surgeon's hands and arms and those of the assistants are exposed to x-ray which presents undesirable health hazards.

(c) The need for assistants during the reduction hinders the full control of the surgeon over the procedure and at the same time adds to the cost of the health care.

In the prior art, fracture reducing devices are well known. Examples include U.S. Pat. No. 4,558,697 (1985), to Wu and U.S. Pat. No. 4,471,768 (1984), to Ciullo. These devices fail to provide satisfactory solution to aforementioned problems. Specifically, in difficult cases where the fragments are continually pulled apart by the muscles, these prior art devices require the surgeon to continuously apply the counteracting forces in order to maintain the achieved reduction, until the fixation is in place. Furthermore, although some prior art devices allow the surgeon's hands to be relatively away from the direct path of x-ray, nevertheless, because the surgeon must continually apply the counteracting forces through these devices and of necessity stand near the limb while x-ray is in use, his hands are still in the vicinity of the x-ray field and do receive some undesirable exposure. Another shortcoming of the prior art devices, especially in cases where fragments are continually pulled apart by the muscles, is that they require assistants to help the surgeon, either in operating the device or in putting the fixation in place while the reduction is being maintained using the device. This need for assistants hinders the full control of the surgeon over the procedure and adds to the cost of the health care.

Accordingly, several objects and advantages of the present invention are:

(a) to provide an apparatus for the orthopedic surgeon to apply large counteracting forces to manipulate and reduce fractures without the need for assistants;

(b) to provide an apparatus which, during every step of the reduction as well as when the full reduction is achieved, can be set by the surgeon to maintain the achieved alignment of bone fragments by itself, thus enabling the surgeon to completely step out of the area of x-ray during the imaging process;

(c) to provide an apparatus which can be set by the surgeon to maintain the achieved alignment of the fragments by itself, thus freeing the surgeon's hands to put in place the cast or the intramedullary fixation as indicated.

SUMMARY OF THE INVENTION

The present invention is a fracture reducing apparatus for achieving and maintaining fracture reduction by the use of leverage mechanisms, having three side arms that are threadedly connected to the two main arms. A knob pivotally connects the two main arms and maintains their relative position with respect to one another. The side arms distribute the counteracting forces from the surgeon's hands to three points along the surface of the fractured limb. During every step of the alignment of the bone fragments and until a full reduction is achieved, the knob is readily tightened to maintain the relative position of the main arms with respect to one another and to maintain the fracture reduction without further intervention of the surgeon, thus freeing the surgeon's hands. Therefore, the apparatus allows for achieving and maintaining reduction without the use of any assistants, and at the same time enables the surgeon to completely step away from the x-ray field, or to apply the fixation, while the apparatus maintains the achieved reduction.

These and other advantages of the present invention may best be understood by reference to the following detailed description and accompanying drawings.

DETAILED DESCRIPTION OF THE INVENTION

Figure 1:
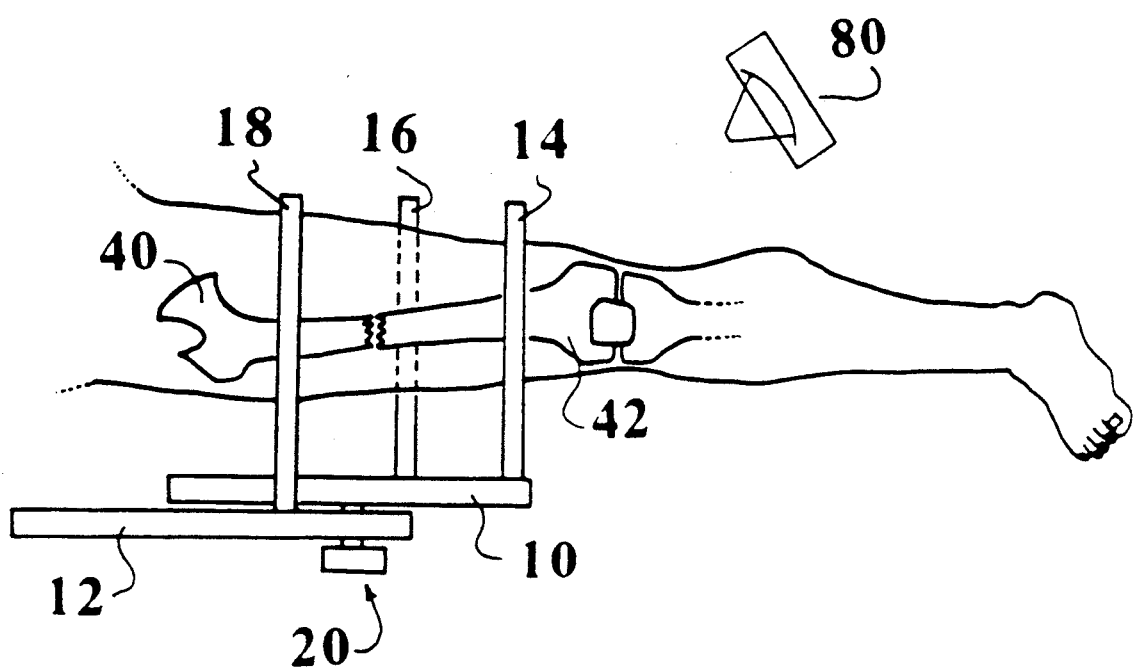
FIG. 1 is a plan view illustrating the application of the present invention in reducing a femur fracture.
Figures 6A, 6B, 6C:
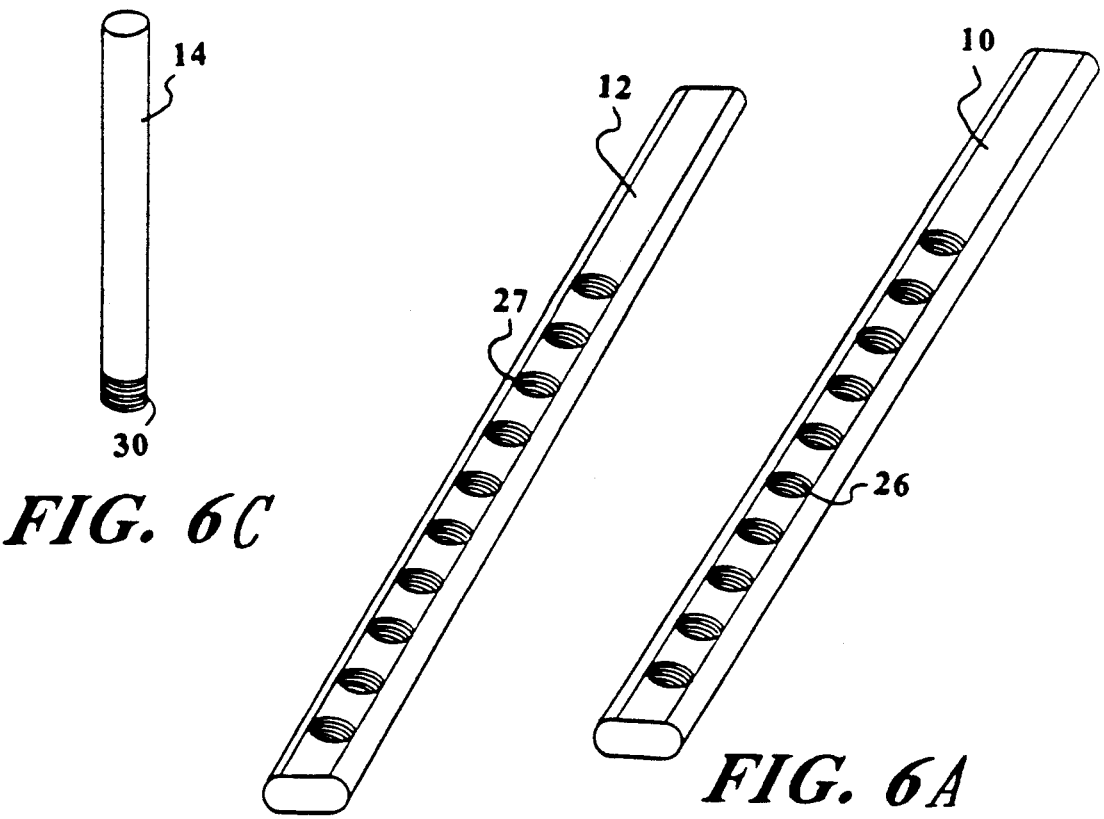
FIG. 6 is a drawing of a preferred embodiment of the components of the Fracture Reducing Apparatus.
Figures 6D, 6E, 6F:
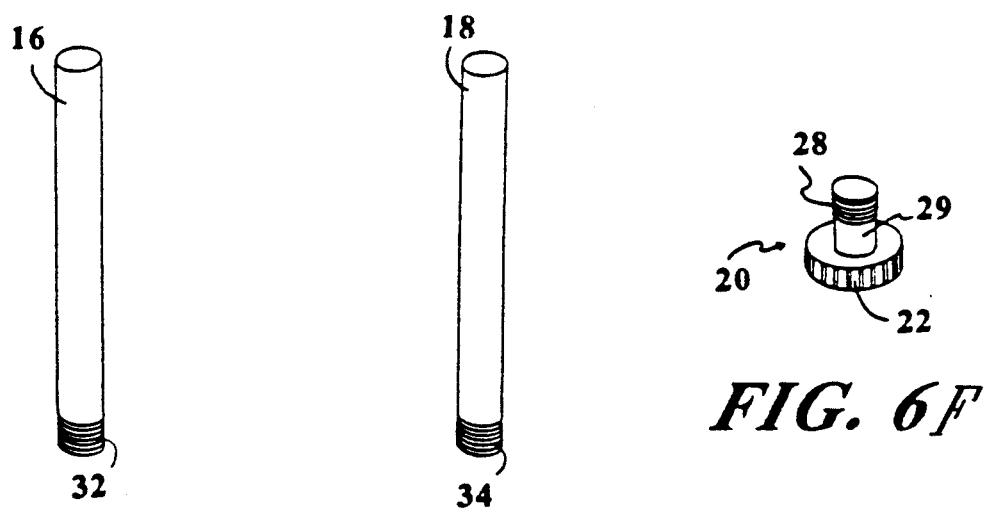

FIG. 1 shows a the application of the present invention in reducing a femur fracture. FIG. 6 is a drawing of a preferred embodiment of the components of the present invention. Referring to FIG. 6, main arms 10 and 12 have a plurality of regularly spaced holes 26 and 27, respectively. As shown, holes 26 and 27 are of the same size, and are bored and threaded perpendicularly to the longitudinal axis of main arms 10 and 12 along the same plane. Side arms 14, 16, and 18, having threaded ends 30, 32, and 34, respectively, are threadedly connected in holes 26, and 27 of main arms 10, and 12. Knob 20 consists of handgrip 22, and unthreaded segment 29, and threaded end 28. Threaded end 28 is threadedly connected in holes 26 and 27 of main arms 10 and 12. Unthreaded segment 29 is of the same diameter as the bore diameter of holes 26 and 27, thus allowing unthreaded segment 29 to pass through holes 26 and 27.

Figure 2:
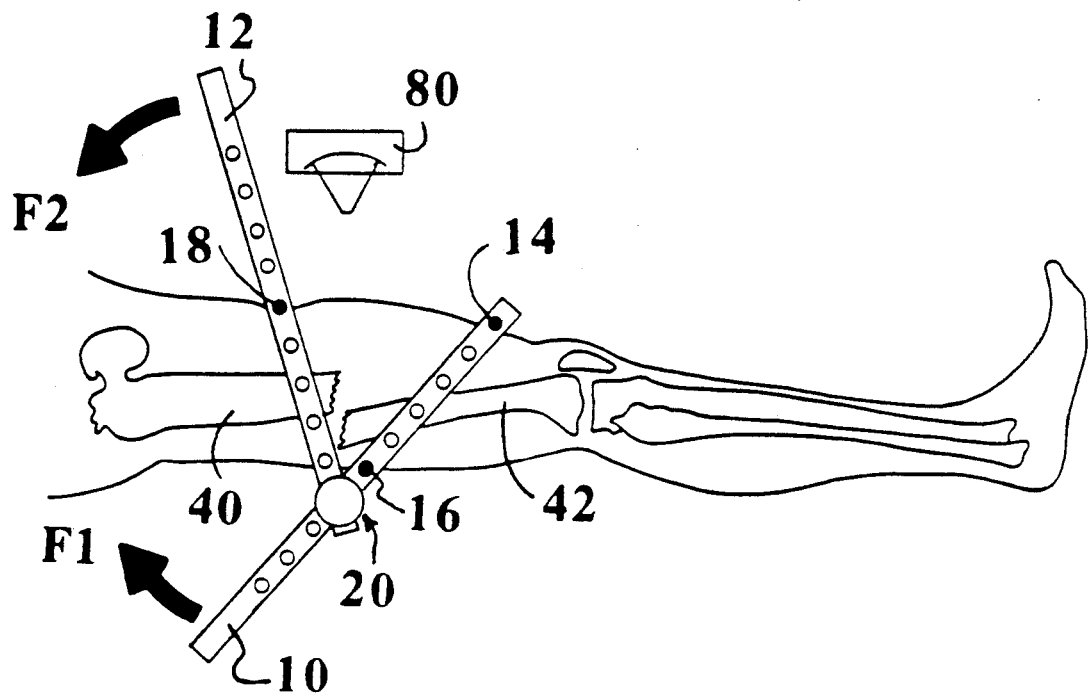
FIGS. 2 and 3 show the application of the present invention in reducing a mid-shaft, oblique, dorsally displaced fracture of the femur.
Figure 3:
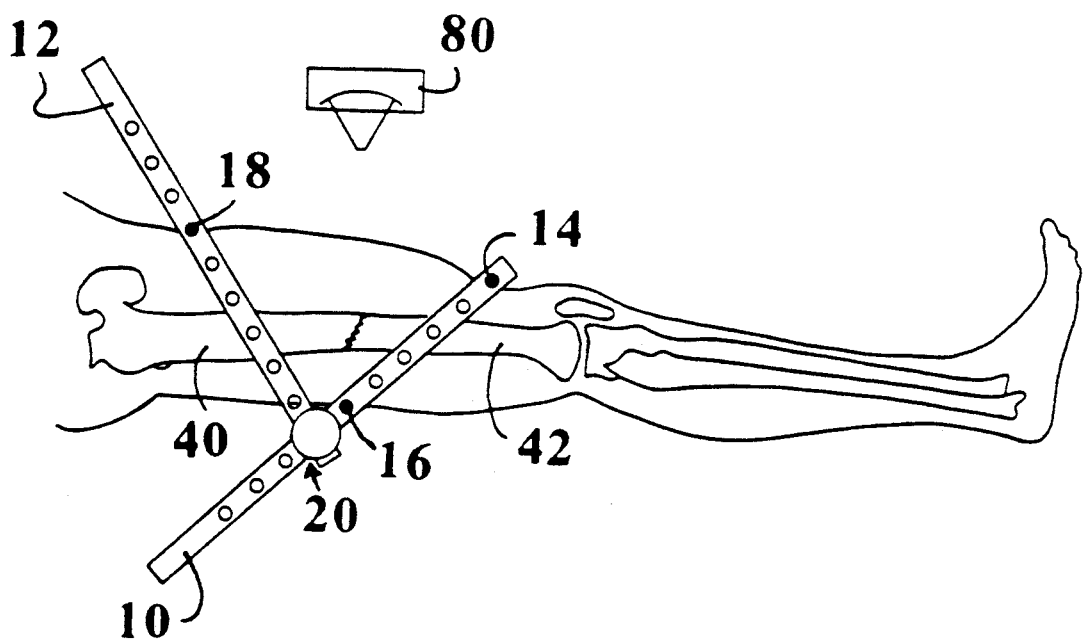

In use, referring to FIGS. 1, 2, and 6, traction is applied to the fractured limb and an x-ray imaging device 80 is used to visualize the fracture. The application of traction and use of x-ray imaging is well known to the art. Side arms 14 and 16 are threadedly connected to main arm 10. The assembly of main arm 10 and side arms 14 and 16 is placed on the limb at the fracture site so that side arms 14 and 16 are on the opposite sides of the limb. Main arm 12 is pivotally connected to main arm 10 by using knob 20, so that threaded end 28 first threadedly engages hole 27 of main arm 12 and then as unthreaded segment 29 passes through hole 27 of main arm 12, threaded end 28 is threadedly connected in hole 26 of main arm 10. Side arm 18 is threadedly connected to main arm 12 so that side arm 18 is at the surface of the limb on the same side as side arm 14. Using hand grip 22, knob 20 is tightened to maintain the relative position of main arms 10 and 12 with respect to one another and the limb, yet allowing the movement of main arms 10 and 12 by forces F1 and F2 exerted by the surgeon to the respective main arms. Main arms 10 and 12 distribute forces F1 and F2 to side arms 14, 16, and 18 which move bone fragments 40 and 42 into the proper alignment. Once full alignment is achieved, as shown in FIG. 3, knob 20 is further tightened to fully restrict any further movement of main arms 10 and 12, allowing the device to maintain the fracture reduction without further intervention of the surgeon. Thus the surgeon's hands would be free to apply the fixation. The fixation is applied in a manner that is well known to the art. Depending on the location, the extent, and the type of the fracture, the fixation may consist of intramedullary nailing, open reduction and internal fixation with various plates and screws, or cast application.

Figure 4:
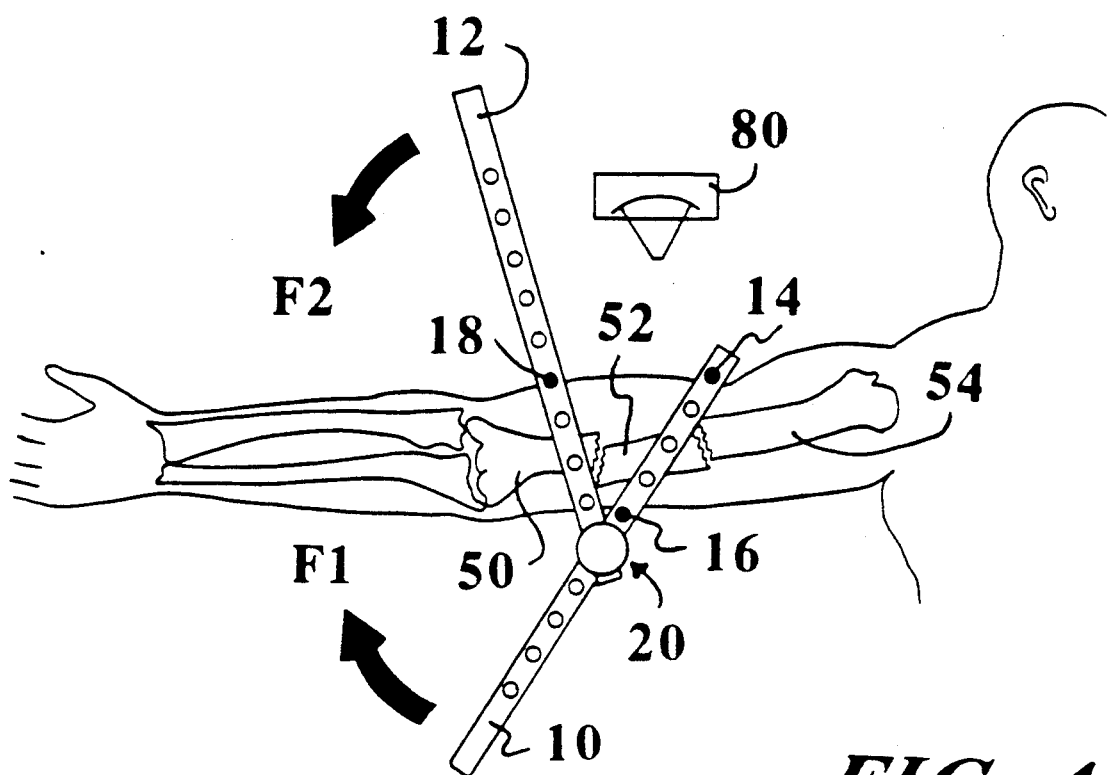
FIGS. 4 and 5 show the application of the present invention in reducing a segmental fracture of the humerus.
Figure 5:
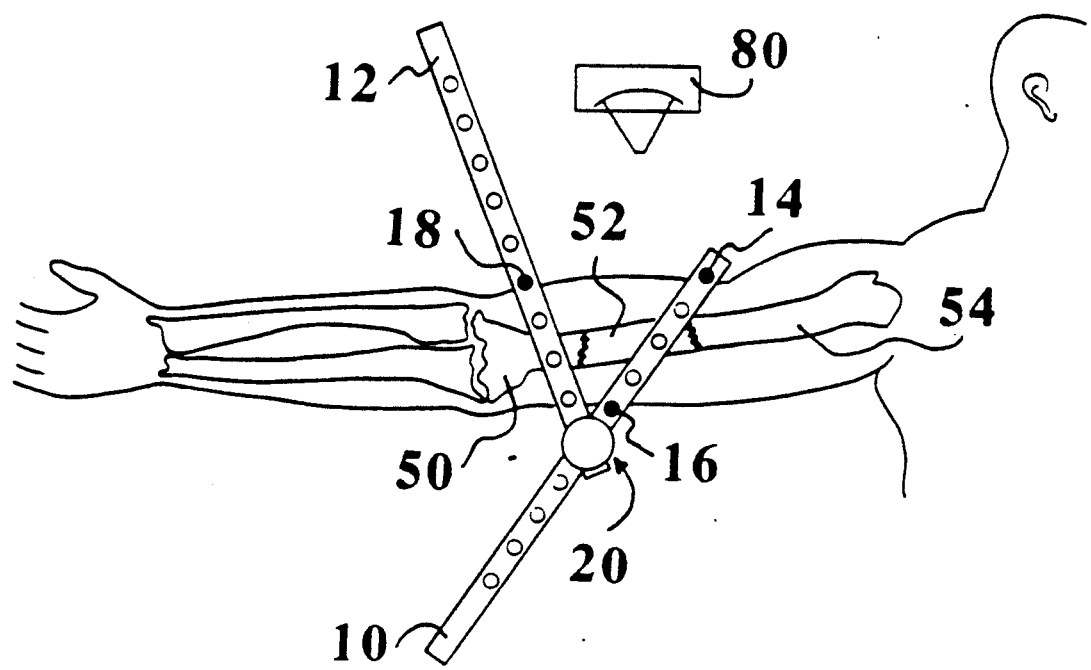

Referring now to FIGS. 4 and 6, traction is applied to the fractured limb and an x-ray imaging device 80 is shown. Side arms 14 and 16 are threadedly connected to main arm 10. The assembly of main arm 10 and side arms 14 and 16 is placed on the limb at the fracture site so that side arms 14 and 16 are on the opposite sides of the limb. Main arm 12 is pivotally connected to main arm 10 by using knob 20, so that threaded end 28 first threadedly engages hole 27 of main arm 12 and then as unthreaded segment 29 passes through hole 27 of main arm 12, threaded end 28 is threadedly connected in hole 26 of main arm 10. Side arm 18 is threadedly connected to main arm 12 so that side arm 18 is at the surface of the limb on the same side as side arm 14. Using hand grip 22, knob 20 is tightened to maintain the relative position of main arms 10 and 12 with respect to one another and the limb, yet allowing the movement of main arms 10 and 12 by forces F1 and F2 exerted by the surgeon to the respective main arms. Main arms 10 and 12 distribute forces F1 and F2 to side arms 14, 16, and 18 which move bone fragments 50, 52, and 54 into the proper alignment. Once full alignment is achieved, as shown in FIG. 5, knob 20 is further tightened to fully restrict any further movement of main arms 10 and 12, allowing the device to maintain the fracture reduction without further intervention of the surgeon. Thus the surgeon's hands would be free to apply the fixation.

While the above description contains many specificities, these should not be construed as limitations on the scope of the invention, but as merely providing illustrations of some presently preferred embodiments of this invention. Many other variations are possible. For example, the main arms or the side arms may have various lengths or shapes, or made of different materials like various metal alloys such as steel for improved durability; or radiolucent materials such as various plastics for improved x-ray imaging of the fracture. Also various combinations of main arms and side arms may be used together or separately, as needed for different types of fractures.

I claim:

1. A fracture Reducing Apparatus for reducing fractures in a human patient, comprising;
 a first arm member having generally flat upper and lower surfaces and having a length greater than its thickness and defining a first longitudinal axis;
 a second arm member having generally flat upper and lower surfaces and having a length greater than its thicknes and defining a second longitudinal axis;
 each of said first and second arm members including a plurality of threaded apertures spaced along the lengths of said first and second longitudinal axes;
 said first arm member including two threaded rods threadingly engaging two of said apertures on said first arm member and a third threaded rod threadingly engaging one of said apertures on said second arm member, each of said rod members having blunt ends for non-puncturing contact with said patient;
 a pivot member having a knob and a shortened threaded rod, said pivot member threadingly engaging apertures on each of said first and second arm members to permit pivotable movement of said members such that when a limb of said patient is placed between said three rod members pivoting of the arm members will cooperatively act to reduce a bone fracture.

* * * * *